US006441202B1

(12) United States Patent
Lightner

(10) Patent No.: US 6,441,202 B1
(45) Date of Patent: Aug. 27, 2002

(54) HETEROCYCLIC COMPOUNDS EXTRACTED BY A HYDROCARBON

(76) Inventor: Gene E. Lightner, 706 SW. 296th St., Federal Way, WA (US) 98023

( * ) Notice: Subject to any disclaimer, the term of this patent is extended or adjusted under 35 U.S.C. 154(b) by 0 days.

(21) Appl. No.: 09/933,439

(22) Filed: Aug. 20, 2001

(51) Int. Cl.$^7$ ............................................. C07D 307/48
(52) U.S. Cl. ....................................... 549/490; 549/489
(58) Field of Search ................................. 549/490, 489

(56) References Cited

U.S. PATENT DOCUMENTS

| | | | |
|---|---|---|---|
| 4,515,680 A | 5/1985 | Hettinger, Jr. et al. | 208/87 |
| 4,612,268 A | 9/1986 | Sherman et al. | 435/157 |
| 4,740,605 A | 4/1988 | Rapp | 549/483 |
| 4,971,657 A | * 11/1990 | Avignon et al. | 549/489 |
| 5,788,812 A | * 8/1998 | Agar et al. | 549/490 |
| 6,054,611 A | * 4/2000 | Farone et al. | 549/489 |

OTHER PUBLICATIONS

Organic Chemistry, 1943, Hill and Kelly, pp. 780–781, p. 778.
ACS Meeting 28, Aug. 2, 1983, Wright, p. 2.
Chemical Process Industries, 2$^{nd}$ edition, 1956, Shreve, p. 840.

* cited by examiner

*Primary Examiner*—Deborah C. Lambkin

(57) ABSTRACT

Sugars derived from acidic hydrolysis of biomass consist of glucose and xyloses which are subjected to dehydration, within the hydrolysis environment, to form heterocyclic compounds, furfural and hydroxymethylfurfural. By providing a vessel for hydrolysis with a supply of a biomass, hydrolysate, containing acid and heterocyclic compounds, is formed. Upon withdrawing the hydrolysate from the vessel, and subjecting the hydrolysate to extracting with a hydrocarbon forms an extractate, containing dissolved heterocyclic compounds within the hydrocarbon, and a raffinate, providing a hydrolysate substantially devoid of heterocyclic compounds for recycle to the hydrolysis vessel. Withdrawing residue remaining from hydrolysis, containing lignins, from the vessel, and subjecting the residue to filtering, resulting in a filtrate for recycle to the vessel and provides filtered residue for subsequent processing. Thereby, heterocyclic compounds are derived from a biomass and withdrawn from the hydrolysis vessel. Residue, remaining from hydrolysis of the biomass, is also withdrawn from the hydrolysis vessel.

20 Claims, 3 Drawing Sheets

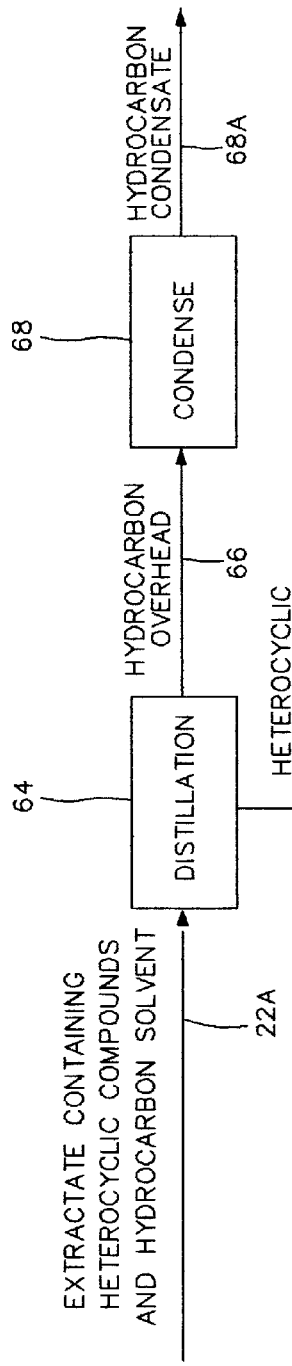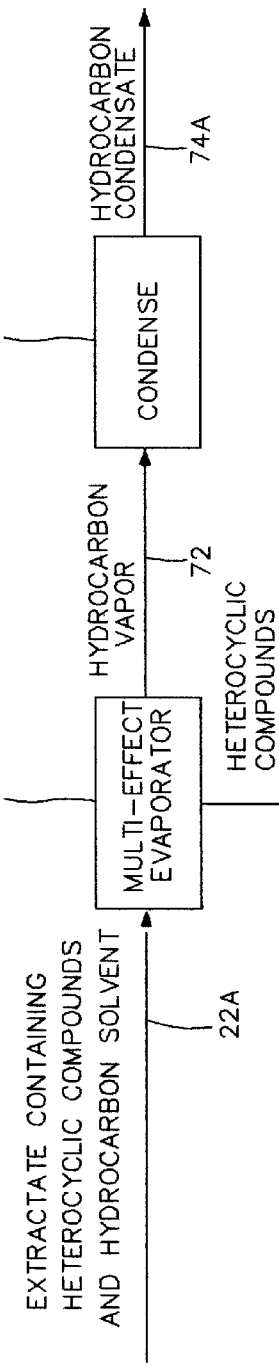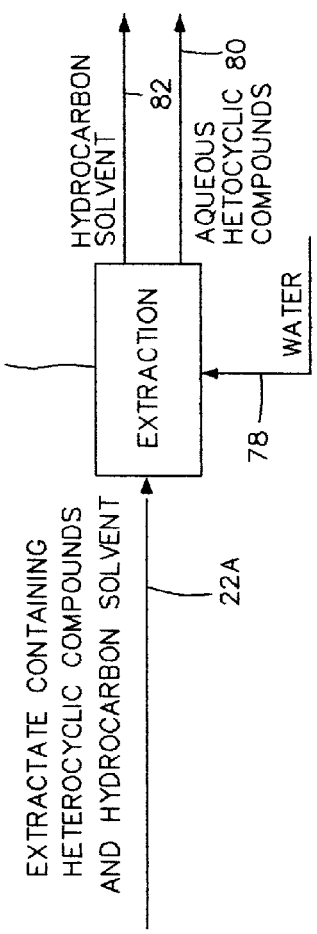

HETEROCYCLIC COMPOUNDS EXTRACTED BY A HYDROCARBON

BACKGROUND OF THE INVENTION

Present day interest in hydrolysis of biomass is to provide an alternative fuel source to avoid dependence on unreliable imported petroleum crude oil for liquid fuels. Characteristic dry biomass composition is: lignin 25%, hemicellulose 25%, amorphous cellulose 10%, and crystalline cellulose 40%. Biomass is selected from the group consisting of wood, waste paper and municipal solid waste including an individual or a combination thereof Acid for hydrolysis is selected from the group consisting of inorganic acids and organic acids including sulfuric acid.

Furfural is produced by hydrolysis of hemicellulose to produce pentose sugars subjected to dehydration to form furfural. Furfural is undesired in a hydrolysate for fermentation because furfural of sufficient concentration in the hydrolysate will substantially inhibit growth of microorganisms required for fermentation, professed by Sherman, et al., in U.S. Pat. No. 4,612,268.

A hydrolysate containing hydroxymethylfurfural derived from dehydration of glucose formed by hydrolysis of a biomass, decreases contents of glucose for fermentation. The unwanted effect of hydroxymethylfurfural and furfural, within the hydrolysate, in providing inhibition of fermentation to produce ethanol within fermentation is contributed by Larsson, et al., on the internet, entitled , "The generation of fermentation inhibitors during dilute acid hydrolysis of softwood."

A state of the art process "process for preparing pure 5-hydroxymethylfuraldehyde" (HMF) is described by Rapp, in U.S. Pat. No. 4,740,605, wherein saccharides are acid catalyzed to form HMF followed by extraction and chromatography to purify HMF.

It is therefore an object of this invention to obviate many of the limitations or disadvantages of the prior art.

The present concern is about producing heterocyclic compounds from a biomass.

A distinct object of this invention is to provide heterocyclic compounds derived from acidic hydrolysis of a biomass.

Still another object of this invention is to provide liquid fuels from a biomass without depending on fermentation.

Yet another object of this invention is to withdraw residue, containing lignins, remaining from hydrolysis of a biomass.

With the above and other objects in view, this invention relates to the novel features and alternatives and combinations presently described in the brief description of the invention.

APPLICATIONS AND BACKGROUND OF THE INVENTION

Heterocyclic compounds such as furfural and hydroxymethylfurfural are derived from acidic hydrolysis of biomass. Heterocyclic compounds having five rings of four carbon atoms and one oxygen atom consisting of furfural and hydroxymethylfurfural are described in Organic Chemistry, 1948, authored by Hill and Kelley, page 778 and pages 780–781 Acidic hydrolysis of biomass, containing henicellulose and cellulose, form xyloses and glucose which are respectively subjected to dehydration, within the hydrolysis environment, to form heterocyclic compounds, furfural and hydroxymethylfurfural.

Hydrolysis of lignocellulose (biomass) kinetics for formation of hydroxymethylfurfural and furfural is described in "High temperature acid hydrolysis of cellulose for alcohol fuel production" by John D. Wright, prepared under task No. 3491, by the Solar Research Institute, Golden Colo. for publication by the American Chemical Society Meeting, Aug. 28 to Sep. 2, 1983, page 2. Hydroxymethylfurfural and furfural, within a hydrolysate, are undesirable compounds accompanying sugars and must be separated prior to fermentation, so stated.

An example of using furfural as a solvent is described on page 840, in Chemical Process Industries, second edition, authored by R. N. Shreve, in which furfural is employed to dissolve lube oil to produce a solution for subsequent separation.

A process for extracting aromatic hydrocarbons employing furfural is claimed within claim 1 and claim 3 disclosed by Hettinger, Jr., et al., in U.S. Pat. No. 4,515,680. Thus furfural, as a solvent for aromatics can be applied in reverse, to utilize an aromatic to extract furfural.

Solvents to dissolve hydroxymethylfurfural and furfural are disclosed in the Merck index, eighth edition, 1968, page 552. Organic solvents capable of dissolving heterocyclic compounds referred to include ether, benzene and chloroform. A solvent capable of dissolving heterocyclic compounds and insoluble in aqueous solutions is selected from the group consisting of organic solvents and aromatic hydrocarbon compounds including an individual or a combination thereof Toluene is such an example. Evaporation can be employed to substantially separate an aromatic hydrocarbon compound from dissolved heterocyclic compounds.

BRIEF DESCRIPTION OF THE INVENTION

The present invention, in its broadest aspect, comprises a method to form heterocyclic compounds from a biomass which constitutes providing a vessel for hydrolysis, and providing a biomass and an acid for hydrolysis to the vessel. Thereupon subjecting biomass to hydrolysis within the vessel, to form glucose and xyloses which are subjected to dehydration, within the hydrolysis environment, to form heterocyclic compounds, furfural and hydroxymethylfurfural within a hydrolysate, containing acid and heterocyclic compounds. Hydrolysate, formed by hydrolysis, by removing is withdrawn from the vessel, and subjected to extracting of heterocyclic compounds from a hydrolysate employing aromatic hydrocarbons for extraction to provide a hydrolysate substantially devoid of heterocyclic compounds for recycle. Residue, remaining from hydrolysis of biomass, is removed from the vessel. The previously withdrawn residue is subjected to filtering resulting in a filtrate of a hydrolysate for recycle and filtered residue, remaining from hydrolysis of biomass, subjected to subsequent processing.

Characteristics of the invention include;

Biomass is subjected to hydrolysis within a vessel to form sugars.

Sugars obtained by hydrolysis are susceptible to dehydration to form hydroxymethylfurfural and furfural.

Heterocyclic compounds are derived from a biomass by hydrolysis within a vessel.

Hydrolysate, containing heterocyclic compounds formed by hydrolysis, is withdrawn from the hydrolysis vessel.

Aromatic hydrocarbons are employed to extract heterocyclic compounds from a hydrolysate containing heterocyclic compounds.

Residue, remaining from hydrolysis of biomass, containing lignins, is removed from the hydrolysis vessel.

Hydrolysis is subjected to temperature control to sustain hydrolysis.

BRIEF DESCRIPTION OF THE DRAWINGS

The features that are considered characteristic of this invention are set forth in the appended claims. This invention, however, both as to its origination and method of operations as well as additional advantages will best be understood from the following description when read in conjunction with the accompanying drawings in which:

FIG. 4 is a flow sheet denoting a method to remove a hydrocarbon solvent from an extractate by distillation FIG. 5 is a flow sheet denoting a method to remove a hydrocarbon solvent from an extractate by a multi-effect evaporator.

FIG. 6 is a flow sheet denoting a method to remove heterocyclic compounds from an extractate.

DETAILED DESCRIPTION OF THE PREFERRED EMBODIMENT

Figure 1:
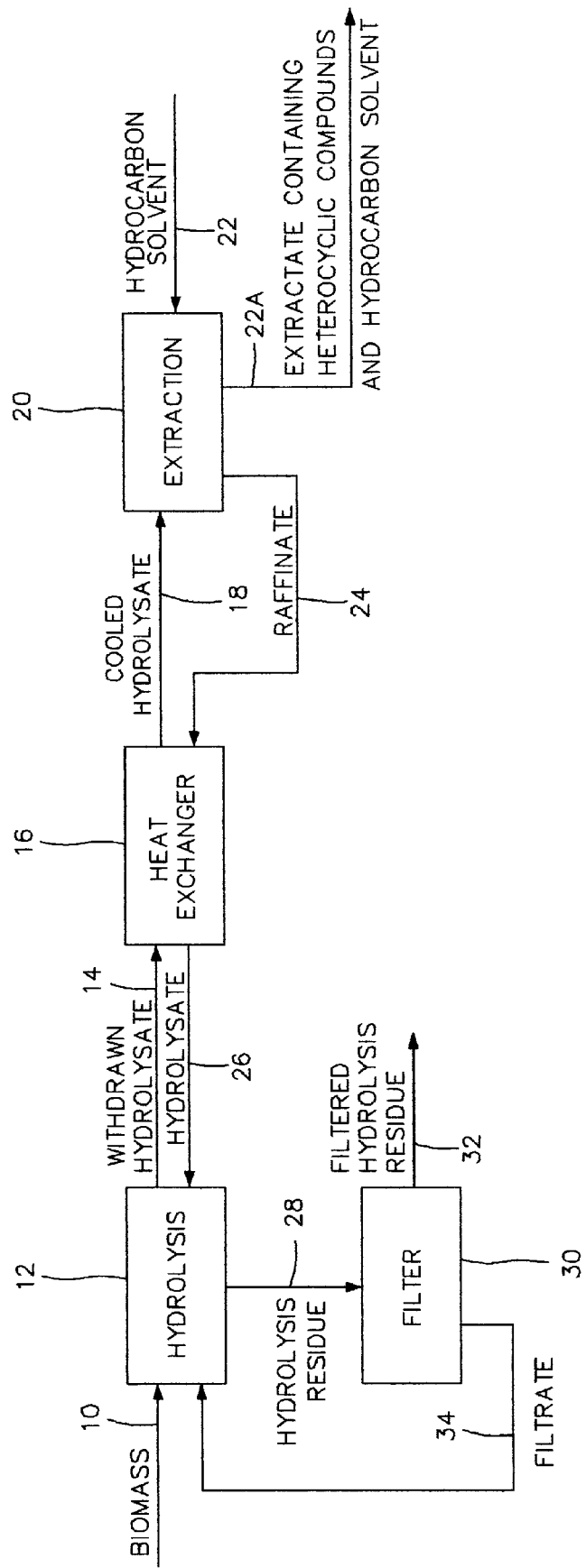
FIG. 1 is a flow sheet denoting the invention as set forth in the appended claims.

The flow diagram of FIG. 1 illustrates the general preferred embodiment of the present invention. In the diagram, rectangles represent stages, operations or functions of the present invention and not necessarily separate components. Details within each stage, operations or functions are not shown. Arrows indicate direction of flow of material in the method. Temperature control is maintained within the vessel from about 100° C. to about 250° C. to sustain hydrolysis. Acid for hydrolysis is usually sulfuric acid at a concentration ranging from of 1 to 10%.

Referring to FIG. 1, a method is depicted to form heterocyclic compounds by hydrolysis of a biomass. Biomass 10 is conveyed to hydrolysis stage 12 and subjected to hydrolysis, forming a hydrolysate 14, which is withdrawn from the hydrolysis stage 12 and conveyed to heat exchanger stage 16 wherein heat is exchanged from raffinate 24 to convey heated hydrolysate 26 to hydrolysis stage 12. Cooled hydrolysate 18 is forwarded to extraction stage 20, extracted by a hydrocarbon solvent 22, to form an extractate containing heterocyclic compounds and hydrocarbon solvent 22A and a raffinate of extracted hydrolysate 24 to be forwarded to heat exchange stage 16. Raffinate 24 is subject to removal of water within FIG. 3. Hydrolysis residue 28 from hydrolysis stage 12 is conveyed to filter stage 30 and subjected to filtration to produce filtrate 34 and filtered hydrolysis residue 32. Filtrate 34 is recycled and conveyed to hydrolysis stage 12. Filtered hydrolysis residue, 32 is subject to additional treatment within FIG. 2. Hydrolysis residue 32 will typically contain lignins. The disclosed method is customarily accomplished in a continuous fashion.

Figure 2:
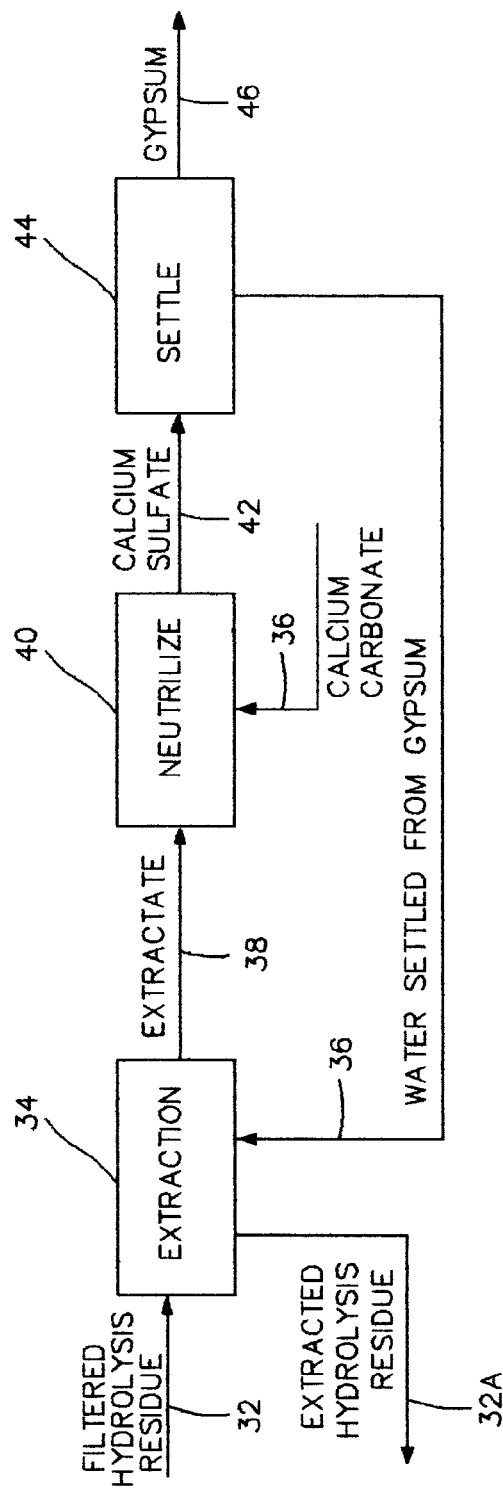
FIG. 2 is a flow sheet denoting a method to extract acid from hydrolysis residue.
Figure 3:
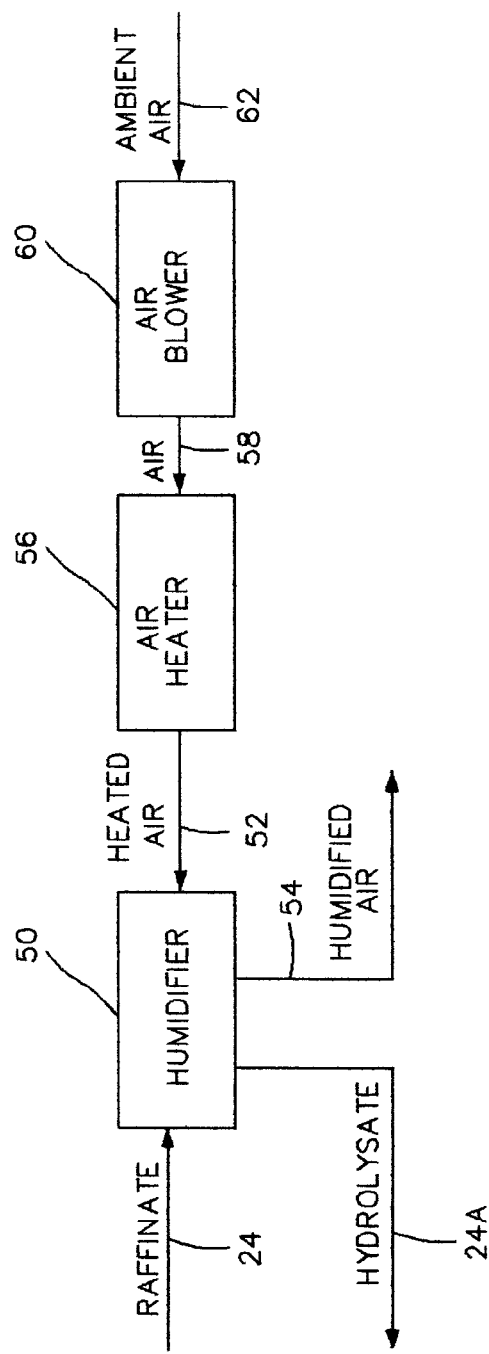
FIG. 3 is a flow sheet denoting a method to remove water from a hydrolysate.

Referring to FIG. 2, filtered hydrolysis residue 32 is conveyed to extraction stage 34 and extracted to produce an extractate 38 and extracted hydrolysis residue 32A. Extractate 38 conveyed to neutralize stage 40 is neutralized by addition of calcium carbonate 36 to create a solution containing calcium sulfate 42 and is conveyed to settle stage 44 to settle and produce gypsum 46 and water 36, settled from gypsum, for recycle to extraction stage 34. Gypsum 46, upon settling, is removed from the settle stage 44 and is discarded. Water 36, settled from gypsum, contains dissolved calcium sulfate and is conveyed to extraction stage 34. Extracted hydrolysis residue 32A, is substantially devoid of acid but contains a trace of dissolved calcium sulfate. The filtered hydrolysis residue 32, containing acid, is substantiality neutralized by chemicals selected from the group consisting of inorganic bases and inorganic salts including an individual or a combination thereof Referring to FIG. 3, raffinate 24 is conveyed to humidifier stage 50 and is humidified by heated air 52, to produce humidified air 54 and hydrolysate 24A to be recycled to heat exchanger stage 16. Heated air 52, is conveyed from air heater stage 56 from flow of air 58 transmited from air blower stage 60 supplied from ambient air 62. Accordingly, water from dehydration within raffinate 24 is removed by air to provide hydrolysate 24A for recycle.

Referring to FIG. 4, extractate containing heterocyclic compounds and hydrocarbon solvent 22A is conveyed to distillation stage 64 and is vaporized to form hydrocarbon overhead 68 and heterocyclic compounds raffinate 64A. Hydrocarbon overhead 66 is conveyed to condense stage 66 to form hydrocarbon condensate 68A. The distillation stage 64 may be operated to produce hydrocarbon overhead 66 substantially free of heterocyclic compounds.

Referring to FIG. 5, extractate containing heterocyclic compounds and hydrocarbon solvent 22A is conveyed to multi-effect evaporator stage 70 and is vaporized to form hydrocarbon vapor 72 and a heterocyclic compounds raffinate 70A. Hydrocarbon vapor 72 is conveyed to condense stage 74 to form hydrocarbon condensate 74A. Hydrocarbon condensate 74A, originating from the multi-effect evaporator stage 70, will transform hydrocarbon vapor into hydrocarbon solvent of reduced heat of vaporization.

Referring to FIG. 6, extractate containing heterocyclic compounds and hydrocarbon solvent 22A is conveyed to extraction stage 76, to be extracted by water 78, to produce aqueous heterocyclic compounds 80 and hydrocarbon solvent 82.

What is claimed is:

1. A method to produce sugars from a biomass by hydrolysis and subject the sugars to dehydration to form heterocyclic compounds which comprises:

providing a vessel with an acid for said hydrolysis, and providing a supply of a biomass to said vessel, and subjecting said biomass, within said vessel, to said hydrolysis to form said sugars, subjected to dehydration, to form a hydrolysate, containing said heterocyclic compounds and said acid, and withdrawing said hydrolysate from said vessel, and extracting the previously withdrawn hydrolysate with a hydrocarbon to form an extractate containing dissolved heterocyclic compounds within said hydrocarbon, and a raffinate, providing a hydrolysate substantially devoid of heterocyclic compounds for recycle to said vessel, and withdrawing residue, remaining from said hydrolysis of said biomass, from said vessel, and filtering said residue resulting in a filtrate for recycle to said vessel and, filtered residue, for subsequent processing, thereby removing heterocyclic compounds, derived from a biomass, from the hydrolysis vessel and removing residue remaining from hydrolysis of biomass from the hydrolysis vessel.

2. The method of claim 1 wherein said hydrocarbon is capable of dissolving said heterocyclic compounds and insoluble in aqueous solutions.

3. The method of claim 2 wherein said hydrocarbon capable of dissolving said heterocyclic compounds and insoluble in aqueous solutions is selected from the group consisting of hydrocarbons and aromatic compounds including an individual or a combination thereof.

4. The method of claim 2 wherein said hydrocarbon capable of dissolving said heterocyclic compounds is toluene.

5. The method of claim 1 wherein said filtered residue, containing acid, is substantiality neutralized by chemicals selected from the group consisting of inorganic bases and inorganic salts including an individual or a combination thereof.

6. The method of claim 1 wherein said filtered residue containing acid is substantiality neutralized by addition of calcium carbonate.

7. The method of claim 1 wherein said heterocyclic compounds include hydroxymethylfurfural and furfural.

8. The method of claim 1 wherein said biomass forms furfural from hemicellulose contained within said biomass.

9. The method of claim 1 wherein said biomass forms hydroxymethylfurfural from cellulose contained within said biomass.

10. The method of claim 1 wherein said acid for said hydrolysis is selected from the group consisting of inorganic acids and organic acids including an individual or a combination thereof.

11. The method of claim 1 wherein said acid for said hydrolysis is sulfuric acid at a concentration ranging from of 1 to 10%.

12. The method of claim 1 wherein said residue remaining from said hydrolysis contains lignins derived from a biomass.

13. The method of claim 1 wherein said extractate containing said hydrocarbon and dissolved heterocyclic compounds is subjected to vaporization.

14. The method of claim 1 wherein said vaporization is by distillation to form an overhead containing said hydrocarbon and a raffinate of said heterocyclic compounds.

15. The method of claim 14 wherein said vaporization is performed by a multiple effect evaporator to form a condensate containing said hydrocarbon and a raffinate of said heterocyclic compounds.

16. The method of claim 1 wherein said hydrolysis is subjected to temperature control to sustain hydrolysis.

17. The method of claim 1 wherein said biomass is selected from the group consisting of wood, waste paper and municipal solid waste including an individual or a combination thereof.

18. The method of claim 1 wherein said heterocyclic compounds are fuels derived from a biomass.

19. The method of claim 1 wherein said method is accomplished in a continuous fashion.

20. The method of claim 1 wherein said extractate containing said hydrocarbon and dissolved heterocyclic compounds is subjected to extraction by water to form aqueous heterocyclic compounds and said hydrocarbon.

* * * * *